United States Patent [19]

Tinti et al.

[11] Patent Number: 5,547,986
[45] Date of Patent: * Aug. 20, 1996

[54] ESTER OF L-CARNITINE WITH GAMMA-HYDROXYBUTYRIC ACID AND PHARMACEUTICAL COMPOSITIONS CONTAINING IT FOR INHIBITING NEURONAL DEGENERATION AND FOR THE TREATMENT OF COMA

[75] Inventors: Maria O. Tinti; Domenico Misiti; Claudio Cavazza, all of Rome, Italy

[73] Assignee: Sigma-Tau Industrie Farmaceutiche Riunite S.p.A., Rome, Italy

[ * ] Notice: The portion of the term of this patent subsequent to Oct. 4, 2014, has been disclaimed.

[21] Appl. No.: 412,858

[22] Filed: Mar. 29, 1995

Related U.S. Application Data

[63] Continuation of Ser. No. 302,995, Sep. 15, 1994, abandoned, which is a continuation of Ser. No. 145,667, Nov. 4, 1993, abandoned, which is a continuation of Ser. No. 991,710, Dec. 16, 1992, abandoned, which is a continuation of Ser. No. 599,995, Oct. 19, 1990, abandoned.

[30] Foreign Application Priority Data

Oct. 20, 1989 [IT] Italy .................. 48475/89

[51] Int. Cl.$^6$ .................................. A61K 31/225
[52] U.S. Cl. .............................. 514/547; 560/170
[58] Field of Search ................. 560/170; 514/547

[56] References Cited

U.S. PATENT DOCUMENTS 4,439,438  3/1984  Cavazza ............................ 560/170

5,041,643  8/1991  Tinti et al. ..

OTHER PUBLICATIONS

Fischer, Ann. Rev. Pharmacol. Toxicol., 26, pp. 161–181 (1986).
Smith, Brain Research Reviews, 13, pp. 103–118 (1988).
Verloes, Psychopharmacology, 95, pp. 226–230 (1988).
Schindler, Prog. Neuro-Psychopharmacol. & Biol. Psychiat., 13, pp. S99–S115, (1988).
"Conn's Current Therapy," Edited by Rakel, pp. 803–807 & 880–886 (1992).
"Cecil Textbook of Medicine," 19th Ed., Edited by Wyngaarden, et al., pp. 2047–2059, 2075–2079 & 2130–2133 (1992).

*Primary Examiner*—Michael L. Shippen
*Attorney, Agent, or Firm*—Oblon, Spivak, McClelland, Maier, & Neustadt, P.C.

[57] ABSTRACT

The L-carnitine ester with gamma-hydroxybutyric acid and its pharmacologically acceptable salts of formula (I)

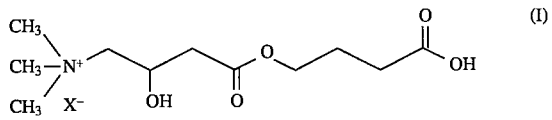

wherein X$^-$ is the anion of a pharmacologically acceptable salt, e.g. chloride, bromide, orotate, acid aspartate, acid citrate, acid phosphate, acid fumarate, lactate, acid maleate, acid oxalate, acid sulfate and glucosephosphate are active in inhibiting neuronal degeneration (as it occurs in Alzheimer's senile dementia and Parkinson's disease) and in the treatment of coma.

7 Claims, No Drawings

ESTER OF L-CARNITINE WITH GAMMA-HYDROXYBUTYRIC ACID AND PHARMACEUTICAL COMPOSITIONS CONTAINING IT FOR INHIBITING NEURONAL DEGENERATION AND FOR THE TREATMENT OF COMA

This application is a continuation of application Ser. No. 08/302,995, filed on Sep. 15, 1994, now abandoned, which is a continuation of application Ser. No. 08/145,667, filed on Nov. 4, 1993, now abandoned, which is a continuation of application Ser. No. 07/1991,710, filed on Dec. 16, 1992, now abandoned, which is a continuation of application Ser. No. 07/599,995, filed on Oct. 19, 1990, now abandoned.

The present invention relates to the L-carnitine ester with gamma-hydroxybutyric acid and its pharmacologically acceptable salts of formula (i)

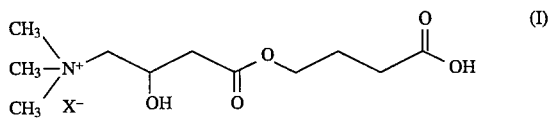

wherein $X^-$ is the anion of a pharmacologically acceptable salt, e.g. chloride, bromide, orotate, acid aspartate, acid citrate, acid phosphate, acid fumarate, lactate, acid maleate, acid oxalate, acid sulfate and glucosephosphate.

These compounds are active in inhibiting neuronal degeneration (as it occurs in Alzheimer's senile dementia and Parkinson's disease) and in the treatment of coma.

The present invention also relates to orally or parenterally administrable pharmaceutical compositions for treating the foregoing pathologies, which comprise one of the compounds of formula (I) as active principle, Whereas, from a theoretical viewpoint, from carnitine and gamma-hydroxybutyric acid three distinct compounds can be obtained, namely:

(i) the salt (ii) a first ester by condensation of the acid OH with the carnitine carboxyl group; and (iii) a second ester, by condensation of the acid carboxyl group with the carnitine OH, the compound of the present invention is the ester (ii), i.e. the compound wherein the ester bond is formed through the carnitine carboxyl group.

Esters of carnitine with hydroxy-substituted saturated organic acids (e.g. 2-hydroxybutyric, 2-hydroxy-2-methylbutyric and 2-methyl-3-hydroxy propionic acid) are known already; see e.g. U.S. Pat. No. 4,766,222 assigned to Sigma-Tau Industrie Farmaceutiche Riunite S.p.A. These compounds, however, are 0-esters (i.e. esters on the carnitine hydroxyl group of type (iii)) and endowed with pharmacological properties entirely different from and in no way related to the properties of the ester of the present invention.

Esters on the carnitine carboxyl group are described in Z. Physiol. Chem., 295, 377, 1953 e Z. Physiol. Chem., 346, 314, 1966. These are, however, esters of carnitine with aliphatic alcohol, such as methanol, ethanol and butanol, or with aromatic alcohols such as benzyl alcohol, not with hydroxy-acids, The example that follows shows the preparation of the ester of L-carnitine chloride with gamma-hydroxybutyric acid via the synthesis scheme which is illustrated on page 5.

EXAMPLE

Preparation of the ester of L-carnitine chloride with gamma-hydroxybutyric acid (ST 701).

STEP A: Preparation of the benzyl ester of gamma-hydroxybutyric acid.

Gamma-bromobutyric acid (3.3 g; 0.02 moles) was suspended in benzyl alcohol (15 ml). The resulting suspension was cooled to 0° C. and thionyl chloride (8 ml; 0.01 moles) was slowly dropwise added thereto. The mixture was kept at room temperature for 16 hours, then concentrated under vacuum in order to remove thionyl chloride and distilled to remove benzyl alcohol. The distillation residue was shown to be the title compound.

TLC Hexane 6 - AcOEt4 $R_f$=0.8

NMR $CDCl_3\delta$((7.2(5H,s,aromatic); 5.0(2H,s,benzyl $CH_2$)3.3(2H,t,$CH_2$COO); 2.6–2.0(4H,m Br$CH_2CH_2$)

STEP B: Preparation of the ester of L-carnitine with gamma-bromo benzylbutyrate.

Carnitine inner salt (0.8 g; 0.005 moles) was suspended in 10 ml anhydrous dimethylformamide. To the suspension gamma-bromobutyric acid benzyl ester (1.3 g; 0.005 moles) was added. The reaction mixture was kept under stirring at 60° C. for 48 hours under a nitrogen stream and then distilled under vacuum in order to wholly remove the solvent; 1.3 g of residue were thus obtained which was shown to be the title product.

TLC $CHCl_3$4.2-$H_2O$ 1.1-Isopr OH 0.7-$CH_3COOH$ 1.1 MetOH 2.8 $R_f$=0.8 NMR $D_2O$ δ 7.4(5H,s,aromatic); 5.2(2H,s,benzyl $CH_2$); 4.6(1H,m,$CH_2C\underline{H}OH$); 4.2(2H.m.O-$CH_2$);3.6(2H.m.N$CH_2$); 3 3(9H,s,$(CH_3)_3$N; 3.0(2H,d,CH-C$\underline{H}_2$COO);2.6(2H,m, $CH_2C\underline{H}_2$COO); 2.0(2H,m,$CH_2C\underline{H}_2CH_2$)

STEP C: Preparation of the ester of L-carnitine bromide with gamma-hydroxybutyric acid.

The product of step B (1.3 g) was dissolved in 20 ml of a $H_2O$-ethanol (1:1 by volume) mixture. The solution was hydrogenated in the presence of 150 mg 10% Pd/C at 3 atmospheres of hydrogen for 2 hours. The mixture was filtered and concentrated under vacuum. One gram of the title product was obtained.

TLC as in step B $R_f$=0.6

STEP D: Preparation of the ester of L-carnitine chloride with gamma-hydroxybutyric acid (ST 701 ).

The product of step C (1 g) was eluted over 30 ml Amberlite IRA 402 strongly basic resin activated to $Cl^-$ form. The eluate was lyophilized. An extremely hygroscopic solid product was obtained. NMR ($D_2O$): δ4.2(2H,t,—$CH_2O$—); 3.5(2H,d,—$N^+CH_2$—); 3.2(9H,s,$(CH_3)_3N^+$); 2,(2H,d,$CH_2$COO); 2.4(2H,m,C$\underline{H}_2$COOH); 2.0(2H,m,C$\underline{H}_2$—$CH_2$COOH).

$[\alpha]_D^{25}$=−13.2 (c=1, $H_2O$)

HPLC

Spherisorb column SCX5M

Eluant: 0.005 M $KH_2PO_4$ —$CH_3CN$ (35–65); pH=4.2

Flow rate: 1 ml/min.

Detector: UV 205 nm

ST 701 $R_T$=7.8

Carnitine $R_T$=10.02 0.5%

Synthesis scheme of L-carnitine chloride with gamma-hydroxybutyric acid (ST 701)

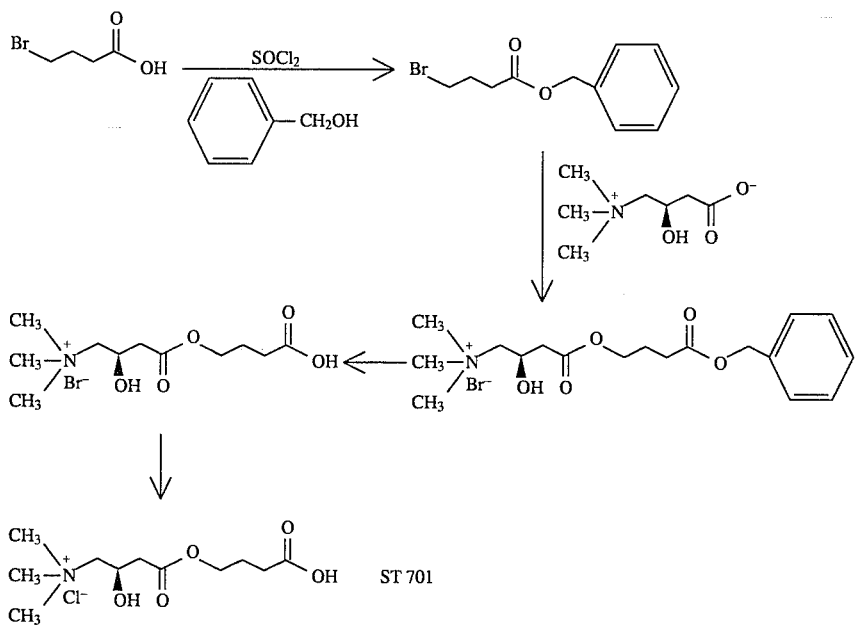

The compounds of the present invention are orally or parenterally administered, in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials.

For these pharmaceutical forms the usual solvents, diluents and excipients are used. Optionally, sweetening, flavouring and preservative agents can also be present. Non limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose at from about 10 to about 50 mg/kg of body weight is preferred. Whenever necessary, larger doses can be safely administered in view of the low toxicity of the compounds of this invention.

As non-limiting examples and depending on the specific pharmaceutical form of administration, the following dosages can be indicated:

| | |
|---|---|
| for the phials | from 5 to 500 mg |
| for the capsules | from 15 to 50 mg |
| for the tablets | from 15 to 500 mg |
| for the oral solutions | from 15 to 50 mg |

We claim:

1. An L-carnitine ester of gamma-hydroxybutyric acid of the formula (I):

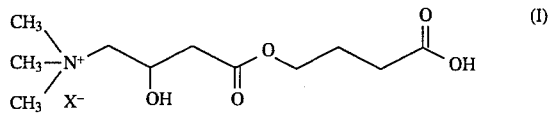

or a pharmacologically acceptable salt thereof, wherein $X^-$ is an anion of a pharmacologically acceptable salt.

2. Ester according to claim 1, wherein $X^-$ is selected from the group consisting of chloride, bromide, orotate, acid aspartate, acid citrate, acid phosphate, acid fumarate, lactate, acid maleate, acid oxalate, acid sulfate and glucosephosphate.

3. A composition comprising the ester of claim 1 or a pharmacologically acceptable salt thereof in an amount effective for the inhibition of neuronal degeneration, and a pharmacologically acceptable excipient.

4. The composition of claim 3, wherein said ester is present in an amount between about 5 and about 500 mg per unit dosage.

5. The composition of claims 3, wherein $X^-$ is selected from the group consisting of chloride, bromide, orotate, acid aspartate, acid citrate, acid phosphate, acid fumarate, lactate, acid maleate, acid oxalate, acid sulfate and glucosephosphate.

6. The composition of claim 3, wherein said pharmacologically acceptable excipient is an orally acceptable excipient.

7. The composition of claim 3, wherein said pharmacologically acceptable excipient is a parenterally acceptable excipient.

* * * * *

UNITED STATES PATENT AND TRADEMARK OFFICE
CERTIFICATE OF CORRECTION

PATENT NO.   : 5,547,986
DATED        : August 20, 1996
INVENTOR(S)  : Maria O. TINTI, et al.

It is certified that error appears in the above-indentified patent and that said Letters Patent is hereby corrected as shown below:

On the title page, Item [*], the Terminal Disclaimer information, should read:

--[*]  The term of this patent shall not extend beyond the expiration date of Pat. No. 5,543,556.--

Signed and Sealed this

Twenty-sixth Day of November 1996

Attest:

BRUCE LEHMAN

Attesting Officer          Commissioner of Patents and Trademarks